United States Patent [19]

Johnson et al.

[11] 4,306,459
[45] Dec. 22, 1981

[54] TRANSDUCER CARRIER FOR ULTRASONIC TESTING

[75] Inventors: Albert S. Johnson; Bruce W. Pappan, both of Ponca City, Okla.

[73] Assignee: Conoco Inc., Ponca City, Okla.

[21] Appl. No.: 121,935

[22] Filed: Feb. 15, 1980

[51] Int. Cl.³ ............................................. G01N 29/04
[52] U.S. Cl. ..................................................... 73/623
[58] Field of Search ........................ 73/623, 637, 640; 33/178 F

[56] References Cited

U.S. PATENT DOCUMENTS 2,736,967  3/1956  Doll ................................... 33/178 F
2,899,633  8/1959  Smith et al. ....................... 33/178 F Primary Examiner—Anthony V. Ciarlante
Attorney, Agent, or Firm—Richard W. Collins

[57] ABSTRACT

A carrier for a plurality of transducers is disclosed. The carrier is useful in ultrasonic testing of furnace tubes. The carrier includes provision for positioning a plurality of transducers against the interior of the tubes.

4 Claims, 5 Drawing Figures

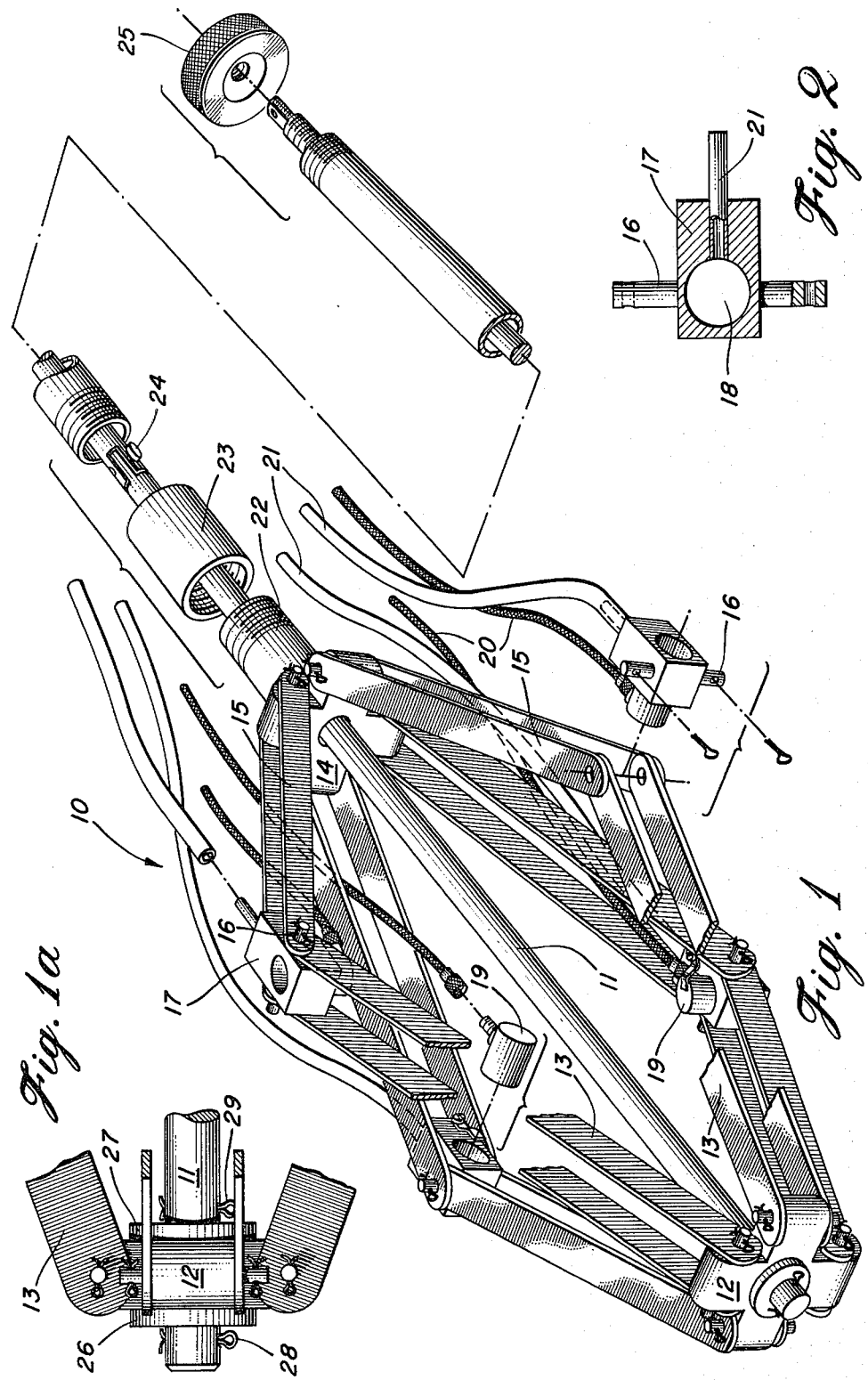

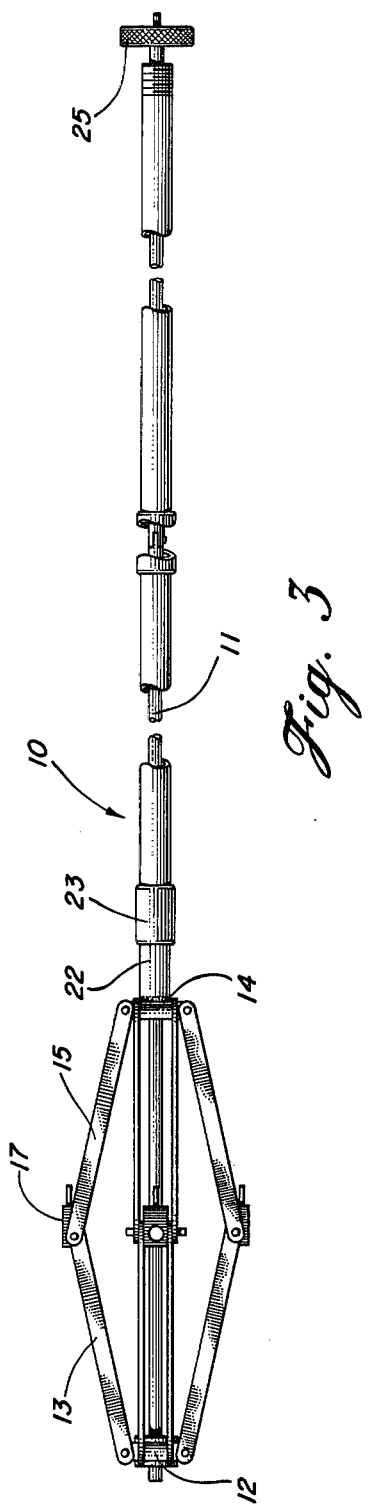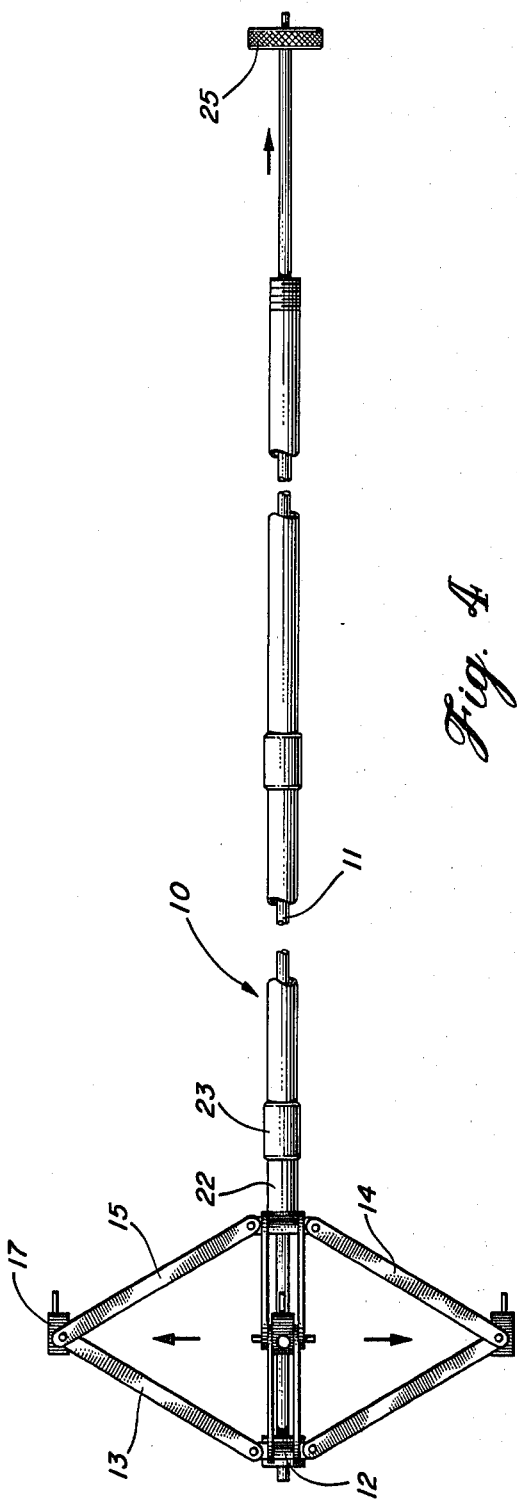

TRANSDUCER CARRIER FOR ULTRASONIC TESTING

BACKGROUND OF THE INVENTION

This invention relates to testing of furnace and boiler tubes or the like using a plurality of ultrasonic transducers inside the tubes, and more particularly relates to an improved transducer carrier which can position ultrasonic transducers against the interior of such tubes for determining their thickness.

Furnace convection tubes and boiler steam tubes are often so closely clustered that their outside walls are inaccessible for conventional ultrasonic thickness inspection such as is described in U.S. Pat. No. 3,741,003.

Several devices have been developed which enable testing of tube wall thickness from the tube interior. U.S. Pat. Nos. 3,021,706 and 3,952,581 and British Patent No. 1,172,385 are exemplary of such devices. More recently, U.S. Pat. No. 4,030,370 issued which describes a transducer positioner for testing tubes from the interior.

The prior art devices described in the above-noted references all are satisfactory to varying degrees, but a need has existed for an improved transducer carrier which is portable and can be used on tubes of widely varying diameters and lengths. Such a carrier is provided by this invention.

SUMMARY OF THE INVENTION

According to the present invention, a transducer carrier is provided which can support a plurality of ultrasonic transducers against the interior of a tube wall. The carrier includes provision for moving the transducers radially outward over a substantial range, so that tubes of different inner diameters can be tested using a single carrier.

The carrier also includes provision for maintaining a water coupling adjacent each transducer, as is conventional.

In one embodiment, the carrier includes provision for adding extensions so that very long tubes can be tested throughout their entire length.

BRIEF DESCRIPTION OF THE DRAWINGS

FIG. 1 is a perspective view, partially exploded and partially cut away, illustrating the carrier of this invention.

FIG. 1a is an enlarged view of the fixed pivot mounting member portion of the carrier.

FIG. 2 is an elevational view, partially in cross-section, illustrating a transducer holder of the type used with the carrier of this invention.

FIG. 3 is a side view illustrating the carrier in its collapsed configuration.

FIG. 4 is a side view illustrating the carrier in its expanded configuration.

DESCRIPTION OF THE PREFERRED EMBODIMENT

The preferred embodiment of the invention as illustrated in the drawings will be described with reference thereto.

Carrier 10 includes an elongated carrier rod 11 having a pivot mounting member 12 affixed to one end. A first group of linkage arms 13 is pivotally mounted to pivot mounting member 12. A movable pivot mounting member 14 is slideably mounted over carrier rod 11, and a second group of linkage arms 15 is pivotally mounted to movable pivot mounting member 14. The first group of linkage arms 13 and the second group of linkage arms 15 are connected together by pivot connections 16 between the fixed and movable pivot mounting members. Pivot connections 16 preferably are extensions of transducer holders 17 (see FIG. 2). In the preferred embodiment shown, four pivot connections are uniformly spaced about carrier rod 11.

Transducer holders 17 include a bore 18 for receiving a transducer 19. Transducers 19 each include an electrical connector 20 (FIG. 1) for transmitting a signal to a readout device (not shown). Transducer holders 17 include a water supply line 21 for providing a water coupling between transducers 19 and the conduit to be tested, all as is conventional and described in detail in the references discussed above.

Movable pivot mounting member 14 is slideably mounted over carrier rod 11, preferably by pipe section 22 welded thereto as shown in FIGS. 3 and 4. Pipe 22, in the preferred embodiment, includes a plurality of sections joined by threaded couplings 23. Carrier rod 11 can include a plurality of sections connected by pins 24 as best seen in FIG. 1.

A large knob 25 is connected to one end of carrier rod 11, such as by threads, for ease of operation in a manner which will be described in detail below.

Fixed pivot mounting member 12 can be attached to carrier rod 11 in any convenient manner, but as illustrated in FIG. 1a, washers 26 and 27 in conjunction with cotter pins 28 and 29 prevent movement of fixed pivot mounting member 12 relative to carrier rod 11.

The operation of the transducer carrier will now be described. With transducers 19 positioned in transducer holder 17 and electrical connectors 20 and water lines 21 aligned toward pipe 22, knob 25 is pushed in toward pipe 22 as shown in FIG. 3 to provide minimum diameter for the linkage arms. The unit is then inserted into a pipe or conduit to be tested, and knob 25 is pulled away from pipe 22. This movement of knob 25 causes fixed pivot mounting member 12 to move toward movable pivot mounting member 14, with resultant movement of pivot connectors 16 outwardly to the position shown in FIG. 4. When transducer holders 17 contact the interior of the pipe to be tested, the unit is activated by providing water flow through lines 21 to create a water column between transducers 19 and the pipe. Readings from the transducers are then taken in a conventional manner, and the carrier is then either rotated through part of a turn or moved longitudinally relative to the pipe and the process repeated.

The carrier of this invention is hand-operated, and in some cases, it may be desirable to clamp carrier rod 11 and pipe 22 to maintain the transducer carriers in position against the interior of the pipe being tested.

In cases where very long pipes are to be tested, additional carrier rod segments can be connected, and additional pipe sections can be joined to pipe 22. The only limitation on the length of the apparatus is the length of the water lines 21 and electrical connectors 20, which must extend beyond the interior of the pipe so that the operator can control the water columns and obtain readings from the transducers.

The technique of testing conduits utilizing ultrasonic transducers does not constitute a part of this invention, as this technology is well-established in the prior art. The present invention, however, provides an improved carrier for placing a plurality of transducers into long conduits or pipes in a convenient manner utilizing a portable, hand-held device which can be adapted to very long lengths of pipe to be tested.

We claim:

1. A carrier for use in determining a physical characteristic of a conduit, said carrier comprising:
   (a) an elongated carrier rod;
   (b) a fixed pivot mounting member rigidly affixed to one end of said carrier rod;
   (c) a first group of linkage arms pivotally connected to said fixed pivot mounting member;
   (d) a movable pivot mounting member slideably mounted over said carrier rod;
   (e) a second group of linkage arms pivotally connected to said movable pivot mounting member;
   (f) pivot connections and transducer holders intermediate said fixed and said movable pivot mounting members linking said first group of linkage arms with said second group of linkage arms, said pivot connections and transducer holders adapted to move radially outward from said carrier rod upon movement of said movable pivot mounting member toward said fixed pivot mounting member; and
   (g) an ultrasonic transducer attached to each of said transducer holders.

2. The carrier of claim 1 wherein a water supply line extends from each transducer holder.

3. The carrier of claim 2 wherein four pivot connections are uniformly spaced about said carrier rod.

4. The carrier of claim 3 wherein said carrier rod is comprised of a plurality of interconnected sections, and a plurality of connected pipe sections extend from said movable pivot mounting member and are slideably mounted over a portion of said carrier rod.

* * * * *